(12) United States Patent
Flather et al.

(10) Patent No.: US 11,571,518 B2
(45) Date of Patent: Feb. 7, 2023

(54) EMERGENCY DEVICES

(71) Applicant: Adamis Pharmaceuticals Corporation, San Diego, CA (US)

(72) Inventors: Mark J. Flather, San Diego, CA (US); Karen K. Daniels, San Diego, CA (US); Thomas Moll, San Diego, CA (US)

(73) Assignee: Adamis Pharmaceuticals Corporation, San Diego, CA (US)

( * ) Notice: Subject to any disclaimer, the term of this patent is extended or adjusted under 35 U.S.C. 154(b) by 752 days.

(21) Appl. No.: 16/422,639

(22) Filed: May 24, 2019

(65) Prior Publication Data

US 2019/0358403 A1 Nov. 28, 2019

Related U.S. Application Data

(60) Provisional application No. 62/676,742, filed on May 25, 2018.

(51) Int. Cl.
| | | |
|---|---|---|
| *A61M 5/28* | (2006.01) | |
| *A61M 5/20* | (2006.01) | |
| *A61K 31/485* | (2006.01) | |
| *A61M 5/31* | (2006.01) | |

(52) U.S. Cl.
CPC .......... *A61M 5/281* (2013.01); *A61K 31/485* (2013.01); *A61M 5/20* (2013.01); *A61M 2005/3125* (2013.01)

(58) Field of Classification Search
CPC ............... A61M 5/20; A61K 31/485
See application file for complete search history.

(56) References Cited

U.S. PATENT DOCUMENTS

| | | | |
|---|---|---|---|
| 4,267,846 A | 5/1981 | Kontos | |
| 5,281,198 A | 1/1994 | Haber et al. | |
| 5,358,489 A * | 10/1994 | Wyrick | A61M 5/002 604/135 |
| 5,713,866 A | 2/1998 | Wilmot | |
| 5,743,887 A | 4/1998 | Brattesani | |
| 6,616,634 B2 | 9/2003 | Benz et al. | |
| 8,627,816 B2 * | 1/2014 | Edwards | A61M 15/08 128/200.14 |
| 9,144,648 B2 * | 9/2015 | Lesch, Jr. | A61M 5/2033 |
| 11,027,072 B2 | 6/2021 | Flather et al. | |

(Continued)

FOREIGN PATENT DOCUMENTS

| | | |
|---|---|---|
| AU | 2012209222 B2 | 2/2012 |
| EP | 2687251 A1 | 1/2014 |

(Continued)

OTHER PUBLICATIONS

International Search Report and Written Opinion dated Jun. 13, 2016, for International Application Serial No. PCT/US2016/022956 filed on Mar. 17, 2016.

(Continued)

*Primary Examiner* — Nathan R Price
*Assistant Examiner* — Melissa A Snyder
(74) *Attorney, Agent, or Firm* — K&L Gates LLP; Louis C. Cullman; Giorgios N. Kefallinos

(57) ABSTRACT

Described herein are syringe devices comprising a syringe including a therapeutic dose of at least one drug to be used in a drug or substance overdose.

22 Claims, 9 Drawing Sheets

(56) References Cited

U.S. PATENT DOCUMENTS

| | | |
|---|---|---|
| 11,141,540 B2 | 10/2021 | Rolfs et al. |
| 2005/0101919 A1 | 5/2005 | Brunnberg |
| 2005/0261634 A1 | 11/2005 | Karlsson |
| 2005/0273054 A1 | 12/2005 | Asch |
| 2007/0017533 A1 | 1/2007 | Wyrick |
| 2008/0103435 A1 | 5/2008 | Graf et al. |
| 2008/0234634 A1 | 9/2008 | Eiland et al. |
| 2012/0217184 A1 | 8/2012 | Edwards et al. |
| 2013/0204229 A1 | 8/2013 | Olson et al. |
| 2015/0051580 A1 | 2/2015 | Shain et al. |
| 2015/0165129 A1 | 6/2015 | Row et al. |
| 2016/0184521 A1 | 6/2016 | Edwards et al. |
| 2021/0290857 A1 | 9/2021 | Flather et al. |
| 2022/0023547 A1 | 1/2022 | Rolfs et al. |

FOREIGN PATENT DOCUMENTS

| | | |
|---|---|---|
| EP | 2874683 B1 | 1/2021 |
| SU | 1727846 A1 | 4/1992 |
| WO | 2011/049713 A2 | 4/2011 |
| WO | 2012/148717 A1 | 11/2012 |
| WO | 2013/071138 A1 | 5/2013 |
| WO | 2013/153121 A2 | 10/2013 |
| WO | 2014/162551 A1 | 10/2014 |
| WO | 2017/034618 A1 | 3/2017 |
| WO | 2019/227061 A1 | 11/2019 |

OTHER PUBLICATIONS

Krieter et al., Pharmacokinetic properties and human use characteristics of an FDA-approved intranasal naloxone product for the treatment of opioid overdose. The Journal of Clinical Pharmacology, vol. 56, No. 10, pp. 1243-1253 (2016).

International Search Report and Written Opinion, dated Aug. 2, 2019, for International Application No. PCT/US2019/034028 filed May 24, 2019.

Extended European Search Report, dated Feb. 4, 2022, for European Patent Application No. 19808355.2.

* cited by examiner

EMERGENCY DEVICES

CROSS REFERENCE TO RELATED APPLICATIONS

This application claims the benefit of U.S. provisional patent application No. 62/676,742, filed May 25, 2018, the entire disclosure of which is incorporated herein by reference.

FIELD

The present invention relates generally to syringes, encasements for syringes, devices including syringes, and methods of using same for emergencies.

SUMMARY

Described herein generally are syringe devices that can deliver a therapeutic dose of a pharmaceutical agent used to treat a drug or substance overdose. In some embodiments, the therapeutic dose can be less than the amount of pharmaceutical agent in the syringe. The devices can also prevent device tampering by a user and/or multiple uses of the same syringe device. In some embodiments, the syringe devices described herein can be used in a critical situation for delivery of an emergency and/or time sensitive pharmaceutical agent in response to a drug or substance overdose. The syringe devices can include a syringe that includes a dose of at least one pharmaceutical agent and can deliver a therapeutic dose of the pharmaceutical agent that can be less than the amount of pharmaceutical agent in the syringe. The syringe can also include a stopper and a gas bubble between the at least one pharmaceutical agent and the stopper. In other embodiments, a gas bubble is not needed and/or desired.

The syringe devices can include an encasement to house the syringe and plunger assembly including a plunger rod, an actuator, and a spacer. In some embodiments, when assembled, the syringe devices can prevent users from tampering with the encased syringe and/or using it for more than one pharmaceutical agent delivery. In some embodiments, the syringe devices can be single use and lock after use.

In various embodiments, the actuator and the spacer can be configured to be secured around the plunger rod. The actuator can include channels and the plunger rod can include protrusions, and the protrusions can be configured to fit within the channels and can provide an adjustable plunger rod location without moving a force application surface.

In some embodiments, the actuator itself can include a finger depression location at the syringe device's force application location instead of force being applied to the plunger rod as in conventional syringes.

The plunger assembly, in some embodiments, can be configured to move the stopper a predetermined distance without a user touching the plunger rod or being able to retract the plunger rod.

In some embodiments, the encasement can be a rigid plastic casing and can include a window configured to allow a user to view the at least one pharmaceutical agent in the syringe to determine if the at least one pharmaceutical agent has or has not expired. A user can tell from potential cloudiness or discoloration if the at least one pharmaceutical agent has expired.

In other embodiments, the encasement can include a needle guard configured to allow the user to cover the needle after use. In such embodiments, the needle guard can slide down from the encasement over the exposed needle to protect from accidental needle sticks after use.

The at least one pharmaceutical agent can be any pharmaceutical agent or combination of pharmaceutical agents described herein. In some embodiments, the pharmaceutical agent(s) can be ones that might be used in an emergency situation to treat a drug or substance overdose. Such pharmaceutical agents can include, but are not limited to naloxone. In some embodiments, a therapeutic amount of these pharmaceutical agents can be about 1 mg to about 100 mg.

Embodiments include syringe devices including a syringe comprising a volume of at least one pharmaceutical agent and a stopper; a plunger assembly including a plunger rod, an actuator, and a spacer. These syringe devices' plunger assemblies can be configured to provide substantially identical doses of the at least one pharmaceutical agent even if more or less pharmaceutical agent is provided in the syringe by moving the stopper a predetermined distance. The volume of the pharmaceutical agent in the syringe can be at least about 0.5 cc.

Also described herein are methods for using the herein-described syringe devices to deliver a pharmaceutical agent(s). Some methods can be for administering a therapeutic dose of at least one pharmaceutical agent. In some embodiments, the administering can be in an emergency to treat a drug or substance overdose. The methods can include advancing a stopper through a syringe including the therapeutic dose of the at least one pharmaceutical agent thereby delivering it to a patient in need thereof.

This advancing can be a predetermined distance. In various embodiments, advancing the stopper the predetermined distance allows a particular amount of pharmaceutical agent to be extruded and/or ejected from the syringe device, for example, through a needle. In some embodiments, the advancing can be configured to deliver about 1 mg to about 100 mg of the at least one pharmaceutical agent to a user and/or patient. Other amounts of pharmaceutical agent can be delivered in other embodiments.

In some embodiments, the actuator and the spacer may be configured to be secured around the plunger rod and provide the predetermined distance between a start point and an end point on the spacer.

DETAILED DESCRIPTION

Figure 1:
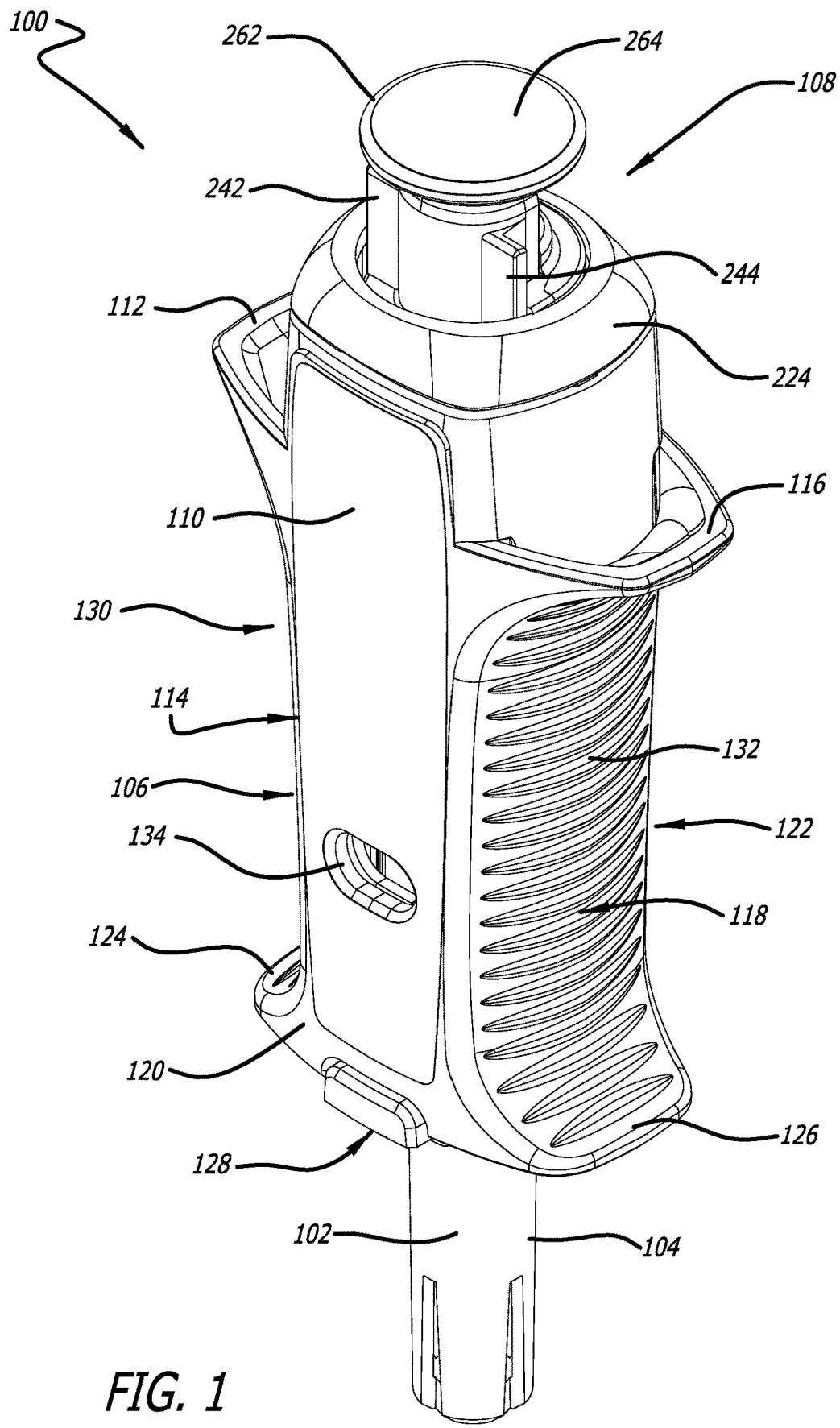
FIG. 1 illustrates a perspective view of a syringe device as described herein.

Described herein generally are syringe devices that allow accurate dosing of a pharmaceutical agent(s), even in situations that require immediate and sometimes rushed interventions in response to a drug or substance overdose. In some embodiments, these situations can be emergency situations where a drug or substance overdose has occurred and time is of the essence.

The syringe devices and/or any accompanying packaging or casing can be sized to be small enough to be portable and/or easily stored. In some embodiments, small size can allow end users to more easily carry the syringe devices and have them available in an emergency situation. In some embodiments, the syringe devices can be stocked in emergency rooms and with emergency medical personnel. Other first responders can also be supplied with syringe devices as described herein. Emergency medical kits can include a syringe device or a syringe device can be deployed when responding to a situation with a drug or substance overdose.

In some embodiments, syringe devices can be supplied at locations where drug and/or substance abuse is likely to occur. For example, syringe devices can be supplied at concerts, parties, clinics, homeless shelters, halfway houses, sober living facilities, and the like.

The syringe devices described herein can allow for current manufacturing tolerances without affecting delivered volume accuracy as will be described herein. A controlled tolerance loop can be used for a delivery stroke in combination with an adjustable plunger rod at the point of secondary packaging. In other words, in some embodiments, volume delivery accuracy does not change if more or less pharmaceutical agent is delivered in a syringe prior to assembly of the syringe device.

Further, features of the syringe devices can prevent outward movement of a plunger rod/stopper under all conditions by means of a mechanical stop. A mechanical stop can prevent outward movement that can introduce air into a needle and/or a syringe that can prevent introduction of a pharmaceutical agent during an emergency drug or substance overdose. The syringe devices can also include a removable locking mechanism. The locking mechanism can be removed prior to use. This removable locking mechanism can prevent inward movement of the plunger rod/stopper up to the point of use.

The syringe devices can also provide tactile feedback to a user at the end of a stroke. This tactile feedback can be useful to inform the user that a dose has been delivered.

Further, the syringe devices can include a locking feature that locks the plunger rod down at the stroke end to assure gas bubble decompression and accurate delivered volume. In some embodiments, a gas bubble is not included and no gas bubble compression exists at the end of a plunger stroke.

The syringe devices can encase a pharmaceutical agent filled syringe such that an end user cannot unscrew or over screw the plunger rod from the stopper and change the travel stroke and thus delivered volume. In some embodiments, a user would have to physically break open the syringe device in order to alter pharmaceutical agent delivery.

Figure 2:
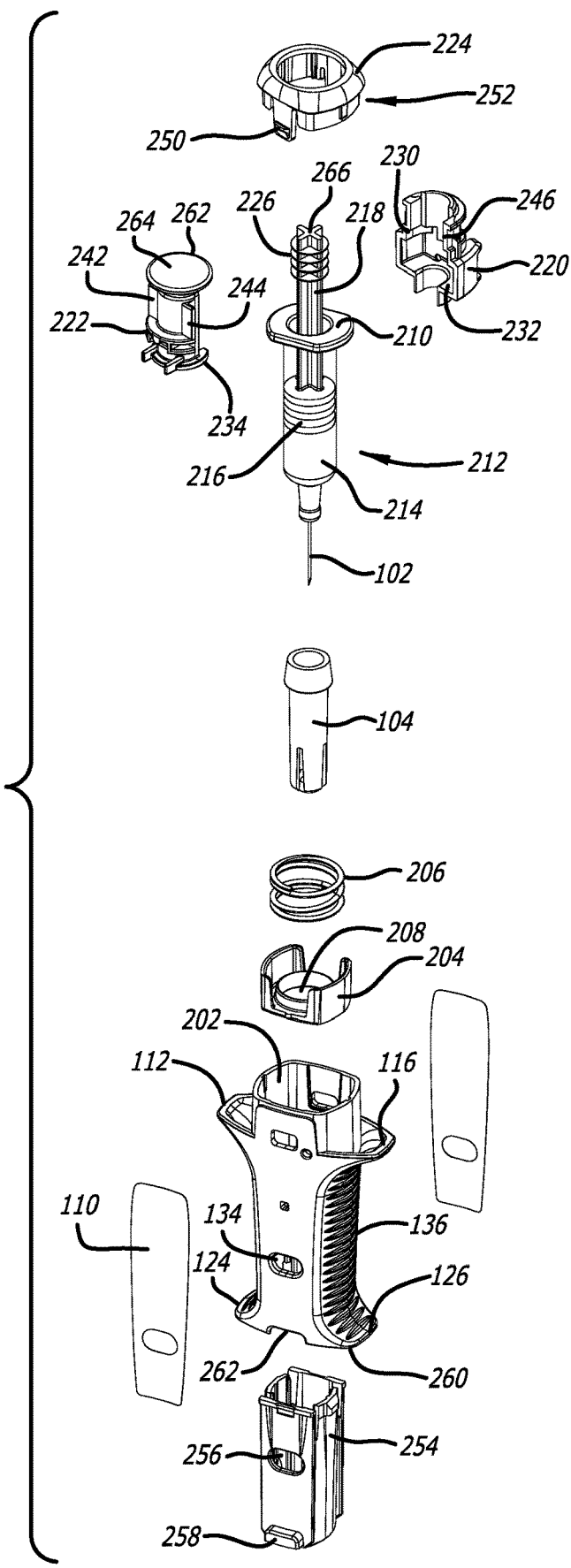
FIG. 2 is an exploded view of the syringe device of FIG. 1.
Figure 3A:
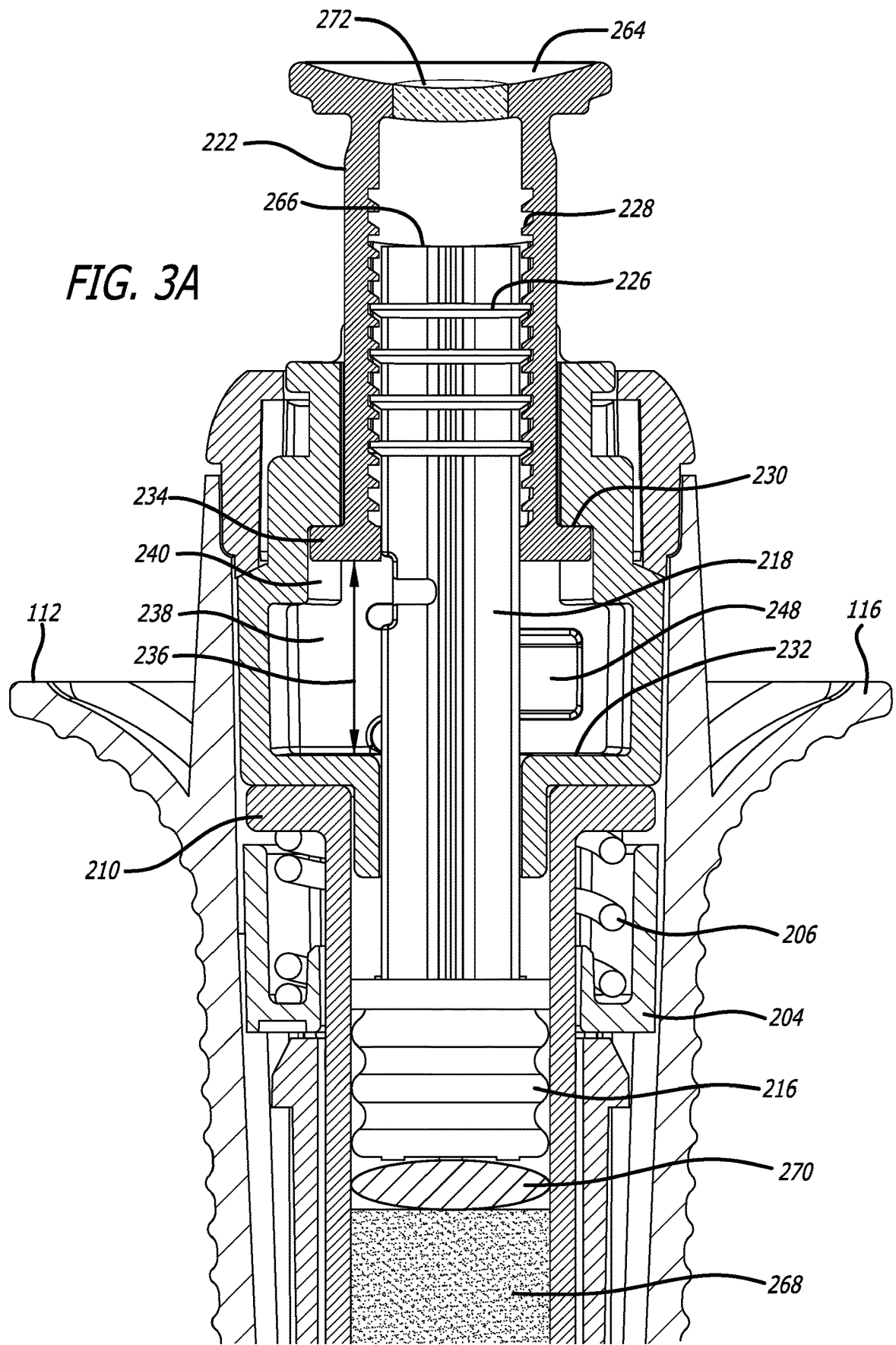
FIG. 3A illustrates a cross-sectional view of the syringe of FIG. 1 with a pharmaceutical agent in the syringe.
Figure 3B:
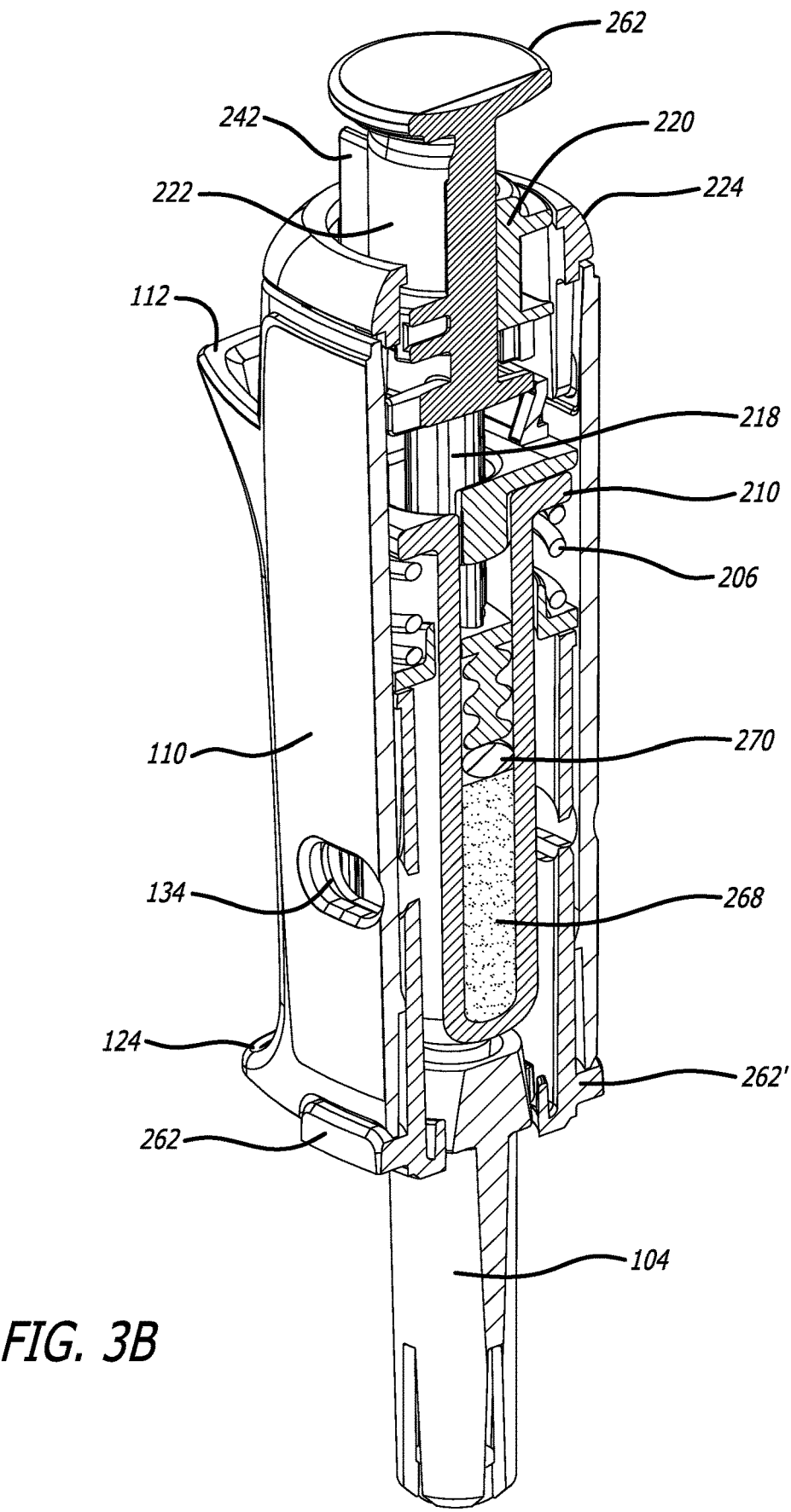
FIG. 3B illustrates another cross-sectional view of the syringe of FIG. 1.

A syringe device can be as illustrated in FIG. 1. FIG. 2 illustrates a cross-section thereof and FIGS. 3A-C illustrate various cross-sections thereof. Syringe device 100 can include a needle 102, a needle guard 104, an encasement 106, and a plunger assembly 108. Encasement 106 and plunger assembly 108 can include many features that will be described in more detail herein.

Encasement 106 can include one or more labels that provide information about the pharmaceutical agent(s) being delivered via syringe device 100. As illustrated in FIG. 1, label 110 can cover substantially an entire surface of encasement 106. However, in other embodiments, label 110 may not cover an entire surface of encasement 106 or multiple labels can be used instead of one large label. In fact, in some embodiments, any number of labels of any shapes can be used to label the product as needed.

Encasement 106 can include any number of flanges. Upper flanges can provide counter balance locations to apply force during injection. Encasement 106 includes a first upper flange 112 on first side 114 and second upper flange 116 on second side 118. Encasement 106 can, in other embodiments, include an upper flange that wraps around the entire perimeter or a substantial portion of the perimeter of encasement 106. However, in the embodiment illustrated in FIG. 1, first upper flange 112 and second upper flange 116 are not on the entire perimeter of top surface 120 of encasement 106 in order to reduce the size of syringe device 100.

Encasement 106 can also include a first lower flange 124 on first side 114 and second lower flange 126 on second side 118. Again, encasement 106 can, in other embodiments, include a lower flange that wraps around the entire perimeter or a substantial portion of perimeter of encasement 106. However, in the embodiment illustrated in FIG. 1, first lower flange 124 and second lower flange 126 are not on the entire perimeter of bottom surface 122 of encasement 106 in order to reduce the size of syringe device 100, In one embodiment, first lower flange 124 and second lower flange 126 create a bottom surface 128. Bottom surface 128, first lower flange 124, and second lower flange 126 can aid with needle insertion by providing a push point. Further, bottom surface 128 with a large surface area provided by the flanges can promote correct orientation with respect to the skin for maximum needle penetration depth.

One or more areas or portions on the face of encasement 106 can include gripping surfaces. Gripping surfaces can include those with textures, perforations, holes, or any other structures that promote grip of syringe device 100. In one embodiment, a gripping surface can be horizontal lines of raised surface. In some embodiments, a gripping surface can be molded into an encasement, and in other embodiments, a gripping surface can be coated in a surface with a high degree of friction, such as rubber. Gripping surfaces or gripping areas can promote easy grasping of syringe device 100 and promote many different syringe holding styles. In one embodiment, a first grip area 130 can exist between first upper flange 112 and first lower flange 124 and a second grip area 132 can exist between second upper flange 116 and second lower flange 126.

Encasement 106 can also include one or more indicia of pharmaceutical agent effectiveness. Indicia can include temperature color change labels that indicate whether the syringe has been subjected to suboptimal temperatures, one or more windows that allow a user to view the pharmaceutical agent within a syringe located within encasement 106, and/or a seal that can be broken prior to use to alert a user whether the syringe had previously been tampered with. In some embodiments, encasement 106 has one or more windows through first side 114, second side 118, or both. In one embodiment, encasement 106 includes a first window 134 on first side 114 and a second window 136 on second side 118. First window 134 and second window 136 can allow a user to view the pharmaceutical agent housed within encasement 106 to see, for example, if a clear solution may be cloudy and hence expired.

An exploded view of syringe device 100 is illustrated in FIG. 2. Within encasement 106 resides several of the syringe device's components. Loaded from distal end 202 of encasement 106 is a syringe stop ring 204 that allows a spring 206 to rest within. Syringe stop ring 204 includes a hole 208 through its body through which a needle 102 and syringe body is inserted through. Spring 206 can rest between syringe stop ring 204 and flange 210 of syringe 212. This arrangement is illustrated in cross-sectional FIGS. 3A and 3B. In some embodiments, syringe flange 210 can be held against spacer 220 by spring 206. If during force of actuation, there is a separation between spacer 220 and syringe flange 210, spring 206 can close this separation after user applied force is removed.

Syringe 212 can include an internal volume 214 that can be filled with one or more pharmaceutical agents. Pharmaceutical agents can be extruded and/or ejected from needle 102 by applying force to stopper 216 by plunger rod 218. Plunger rod 218 can come bonded to stopper 216 or can be screwed into or otherwise attached to stopper using any means known in the art.

Plunger rod 218 is part of plunger assembly 108. Plunger assembly 108 includes plunger rod 218, spacer 220, actuator 222, and top 224. Plunger rod 218 can include multiple protrusions 226 that can interact with channels 228 within inner surface of actuator 222. Protrusions 226 can lock actuator 222 to plunger rod 218.

Spacer 220 is used as a top stop 230 and a bottom stop 232 for actuator ring 234. Top and bottom stops control the amount of stopper travel through syringe 212 and hence the precise amount of pharmaceutical agent extruded and/or ejected from needle 102. Distance 236 can be defined between top stop 230 and bottom stop 232. Distance 236 can be about 4 mm, about 5 mm, about 6 mm, about 7 mm, about 8 mm, about 9 mm, about 10 mm, about 12 mm, about 14 mm, about 16 mm, about 18 mm, about 20 mm, about 22 mm, about 24 mm, between about 1 mm and about 24 mm, between about 4 mm and about 14 mm, or between about 10 mm and about 24 mm.

Distance 236 includes travel distance through spacer cavity 238 and distance through spacer cavity bore 240. Spacer cavity bore 240 includes a partial internal diameter that fits the outer partial diameter of actuator ring 234. In some embodiments, spacer cavity 238 includes an internal diameter that is larger than the outer partial diameter of actuator ring 234. Thus, in some embodiments, when actuator ring 234 is advanced out of spacer cavity bore 240 into spacer cavity 238, it encounters an area where actuator ring 234 is not guided by the fit in spacer cavity bore 240. In order to account for the travel through spacer cavity 238, actuator 222 includes at least one guide rail to prevent rotation(s) and/or alignment issues when advancing actuator 222. In one embodiment, actuator 222 includes first guide rail 242 and second guide rail 244. First guide rail 242 and second guide rail 244 travel against front face 246 of spacer 220.

In some embodiments, distance 236 can be changed, for example reduced, by increasing the thickness of actuator ring 234. Likewise, distance 236 can be increased by reducing the thickness of actuator ring 236. By increasing the thickness of an actuator ring, the amount of distance traveled between top stop 230 and bottom stop 232 can be reduced resulting in less volume of pharmaceutical agent being extruded and/or ejected from needle 102. Such reduced travel distances can be used with smaller patients that require less pharmaceutical agent to treat a particular symptom of drug or substance overdose. For example, in some embodiments, in an emergency drug or substance overdose situation, the patient may have a thin or lightweight build from years of abuse.

In some embodiments, distance 236 can be changed by decreasing the distance between top stop 230 and bottom stop 232 without changing the thickness of actuator ring 234. By adjusting, e.g., increasing or decreasing, the distance between top stop 230 and bottom stop 232, the amount of distance traveled between top stop 230 and bottom stop 232 can be changed resulting in more or less volume of pharmaceutical agent being extruded from needle 102.

In embodiments, distance 236 can be changed by combinations of adjusting the thickness of actuator ring 234 and adjusting the distance between top stop 230 and bottom stop 232.

Actuator 222 can be adjusted relative to plunger rod 218 based on filling variability. FIGS. 3A and 3B illustrate this. In other words, regardless of the volume of pharmaceutical agent in a particular syringe (and hence a location of stopper 216 relative to flange 210), actuator 222 and stopper 220 can be attached to plunger rod 218 and provide an accurate pharmaceutical agent volume delivery.

In one embodiment, if a syringe is provided with too much pharmaceutical agent volume, the actuator and the spacer can be attached around the plunger rod such that protrusions 226 are at a higher location in channels 228. In such an embodiment, the ultimate delivered volume would be the same as if the syringe was provided with less pharmaceutical agent volume.

This changeability of plunger assembly can allow variability in fill volume without having to change manufacturing processes to accommodate different and/or inaccurate fills. The changeability allows for a particular volume of pharmaceutical agent to be extruded and/or ejected from needle 102 regardless of the actual fill volume in the syringe.

In some embodiments, a snap 248 is located at bottom stop 232 to lock plunger rod 218 down via actuator ring 234 at the end of an injection stroke. This lock prevents attempted multiple uses of a syringe. In essence, the lock allows a syringe to be a single use, disposable syringe.

Top 224 includes a hole through it to allow the assembled plunger rod 218, spacer 220 and actuator 222 to protrude at least partially. Top 224 includes at least one tooth, such as first tooth 250 and second tooth 252 to snap into portions of encasement 106. After top 224 is locked into encasement 106, it acts to lock spacer 220 into place by wedging spacer 220 between top 224 and syringe flange 210.

In some embodiments, spacer 220, actuator 222, and top 224 can be keyed to encasement 106 to prevent rotation of the components once assembled.

In some embodiments, syringe device 100 can include a needle guard 254. Needle guard 254 can be manually deployed. Needle guard 254 can include at least one hole 256 that can align with a window on encasement 106 when the needle guard has not been manually deployed. Needle guard 254 can be deployed to aid in injury prevention after use of syringe device 100.

Needle guard 254 can be manually deployed by applying pressure to and pulling on one or more tabs 258 away from proximal end 260 of encasement 106. Proximal end 260 includes indentations 262 to allow full retraction of needle guard 254 into encasement 106. Once fully deployed, needle guard 254 can lock into place preventing needle 102 from being used further or accidentally lancing a human handling the used syringe. This may be particularly important when treating a drug abuser that may have illness or disease acquired from the drug abuse, such as but not limited to HIV and AIDS.

In some embodiments, the needle guard can automatically retract after a dose of pharmaceutical agent has been delivered to a patient. As the user retracts the needle from the patient, needle guard 254 deploys from encasement 106. Deployment can be through a spring force unlocked when force is placed on proximal end 260 of encasement 106 during an injection. Thus, when pulling device 100 away from a patient's skin, needle guard 234 can deploy. In other embodiments, a button can be pressed to begin deploying needle guard 254. The button can simply release a spring force that snaps needle guard into place preventing an accidental needle stick.

Actuator 222 can further include a force application surface 262 at its distal end. Force application surface 262 can be a concave surface 264 promoting user comfort during actuation of the syringe devices. Further, in some embodiments, force application surface 262 can be textured to aid in user feeling when using the syringe devices.

In some embodiments, force application surface 262 can be transparent, such as including a window 272 provided by a material allowing a user to see the top of plunger rod 218. Window 272 can be through the entirety of force application surface 262, particularly at apex of concave surface 264 or otherwise in the center thereof.

The top of plunger rod 218 can include an indication surface 266. Indication surface 266 can be unique to the pharmaceutical agent included in device 100. In some embodiments, indication surface 266 can include raised features such as shapes or can include words or images applied to the surface.

This windowed configuration can prevent label tampering, because the indication surface 266 is internal to the device.

As further illustrated in FIGS. 3A and 3B, internal volume 214 includes a liquid pharmaceutical agent 268. Existing between liquid pharmaceutical agent 268 and stopper 216 can be a gas bubble 270. Gas bubble 270 can be virtually any gas that can occupy the space required between the liquid pharmaceutical agent and the stopper. In some embodiments, a gas bubble is not included.

In some embodiments, the liquid pharmaceutical agent may be substituted with a semisolid or gel pharmaceutical agent. In some embodiments, a pharmaceutical agent delivery vehicle can be used that can be extruded from the needle.

In some embodiments, the gas can be an inert gas such as, but not limited to argon, nitrogen, helium, and the like. In one embodiment, the gas bubble is nitrogen. In some embodiments, the devices described herein do not include a gas bubble. In other embodiments, the gas bubble is not needed as the end of a plunger stroke may not deplete the volume of liquid in the syringe.

Pharmaceutical agents housed in syringe 212 can include any compound having a therapeutic effect in a mammal that is experiencing a symptom of a drug or substance overdose. In some embodiments, the drug overdose is from an illegal or recreational drug. In some embodiments, the substance overdose is from an illegal or recreational substance such as, but not limited to, alcohol, smoke, or the like.

Mammals can include humans, equines, canines, felines, bovines, and the like. In one embodiment, an mammal can be a human.

Non-limiting pharmaceutical agents can include a narcotic blocker, an opioid blocker, or a combination thereof. In some embodiments, salts, prodrugs, derivatives and/or analogues of the herein described pharmaceutical agents can be provided alone or in combination.

In some embodiments, pharmaceutical agent(s) included in the herein described syringes can be used to treat a symptom of a drug or substance overdose or the overdose itself. The pharmaceutical agent(s) included in the herein described syringes can be used to treat symptoms such as difficulty breathing, shortness of breath, breathlessness, tightness of throat, slow heartbeat, no heartbeat, weak pulse, dizziness, passing out, blackout, unconsciousness, itching, swelling, itching in the throat, swelling in the throat, vomiting, diarrhea, cramps, or combinations thereof. In some embodiments, the pharmaceutical agent(s) included in the herein described syringes can be used to treat combinations of the above symptoms in an overdose. In still other embodiments, the pharmaceutical agent(s) included in the herein described syringes can be used to treat other symptoms and/or conditions in an emergency situation.

In one embodiment, the pharmaceutical agent is naloxone, salts thereof, derivatives thereof, and/or prodrugs thereof. In one embodiment, naloxone is provided as a HCL dihydrate.

Naloxone, salts thereof, derivatives thereof, and/or prodrugs thereof can be present at a concentration of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 22 mg/mL, about 24 mg/mL, about 26 mg/mL, about 28 mg/mL, about 30 mg/mL, about 40 mg/mL, about 50 mg/mL, about 60 mg/mL, about 70 mg/mL, about 80 mg/mL, about 90 mg/mL, about 100 mg/mL, between about 5 mg/mL and about 15 mg/mL, between about 10 mg/mL and about 20 mg/mL, between about 10 mg/mL and about 100 mg/mL, between about 1 mg/mL and about 100 mg/mL, between about 50 mg/mL and about 100 mg/mL, at least about 4 mg/mL, at least about 8 mg/mL, at least about 15 mg/mL, at least about 25 mg/mL, or at least about 50 mg/mL. In other embodiments, naloxone, salts thereof, derivatives thereof, and/or prodrugs thereof can be included in syringes described herein to deliver about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 30 mg, about 40 mg, about 50 mg, about 60 mg, about 70 mg, about 80 mg, about 90 mg, about 100 mg, between about 1 mg and about 20 mg, between about 5 mg and about 15 mg, between about 1 mg and about 100 mg, between about 1 mg and about 50 mg, between about 10 mg and about 100 mg, between about 50 mg and about 100 mg, between about 25 mg and about 50 mg, at least about 1 mg, at least about 5 mg, at least about 10 mg, at least about 15 mg, at least about 20 mg, or at least about 50 mg of naloxone in a single injectable dose even if more than that amount is present in the syringe prior to assembly of a syringe device.

In some embodiments, the concentration or dose of naloxone can be administered using a single syringe devices. In other embodiments, the concentration or dose of naloxone can be administered using two or more syringe devices.

In one embodiment, a drug as described herein, salts thereof, derivatives thereof, and/or prodrugs thereof can be in a formulation with a carrier. The formulation can include the drug(s), a salt thereof, derivatives thereof, or prodrugs thereof, one or more tonicity adjuster(s) such as e.g. sodium chloride or other salts, an acid or base to adjust pH, such as e.g. hydrochloric acid or sodium hydroxide, and a solvent or carrier. In some embodiments, the formulation can be in an aqueous formulation and can also include an antioxidant. The antioxidant can be Na-metabisulfite or any other appropriate antioxidant. In still other embodiments, formulations can include an excipient(s) such as but not limited to, a preservative(s), a sorbent(s), a lubricant(s), a vehicle, or the like.

In one embodiment, naloxone, salts thereof, derivatives thereof, and/or prodrugs thereof can be in a formulation with a carrier. The formulation can include naloxone, a salt thereof, derivatives thereof, or prodrugs thereof, one or more tonicity adjuster(s) such as e.g. sodium chloride or other salts, an acid or base to adjust pH, such as e.g. hydrochloric acid or sodium hydroxide, and a solvent or carrier.

In some embodiments, the formulation can be in an aqueous formulation and can also include an antioxidant. The antioxidant can be Na-metabisulfite or any other appropriate antioxidant. In still other embodiments, formulations can include an excipient(s) such as but not limited to, a preservative(s), a sorbent(s), a lubricant(s), a vehicle, or the like.

In some embodiments, the carrier is aqueous. In one embodiment, the carrier is water for injection.

The salt included in a formulation can be any salt. In one embodiment, the salt is sodium chloride, potassium chloride, calcium chloride, ammonium chloride, glycyrrhizic acid, mesitylene sulfonate sodium, chondroitin sulfate, potassium sulfate, monensin sodium salt, sodium hyaluronate, glutamic acid sodium salt, sodium benzoate, magnesium sulfate, or a combination thereof.

In some embodiments, a salt can be included in a formulation to provide an appropriate tonicity.

The acid used to adjust the pH of the formulation can be any acid. In one embodiment, the acid is hydrochloric acid.

In one embodiment, every 1 mL of a formulation can include 5 mg of naloxone.

In one embodiment, every 0.5 mL of a formulation can include 5 mg of naloxone.

In another embodiment, every 1 mL of a formulation can include 15 mg of naloxone.

In another embodiment, every 0.5 mL of a formulation can include 15 mg of naloxone.

In one embodiment, a drug formulation is provided that includes naloxone, sodium chloride, water for injection, and hydrochloric acid as needed to adjust pH. In another embodiment, a drug formulation is provided that includes 2.2 g of naloxone, 1.67 g of sodium chloride, 200 g of water for injection, and 1% hydrochloric acid as needed to adjust pH. In some embodiments, 1 g of naloxone HCl is equivalent to 1.11 g of naloxone HCL dihydrate and is adjusted for purity.

In some embodiments, the drugs can be filled into the syringes in a particular or specific amount. That particular amount can be about 0.2 cc, about 0.3 cc, about 0.4 cc, about 0.5 cc, about 0.6 cc, about 0.7 cc, about 0.8 cc, about 0.9 cc, about 1 cc, about 2 cc, between about 0.4 cc and about 0.6 cc, between about 0.1 cc and about 1 cc, between about 0.3 cc and about 0.7 cc. In one embodiment, the filling volume can be about 0.5 cc.

Figure 4:
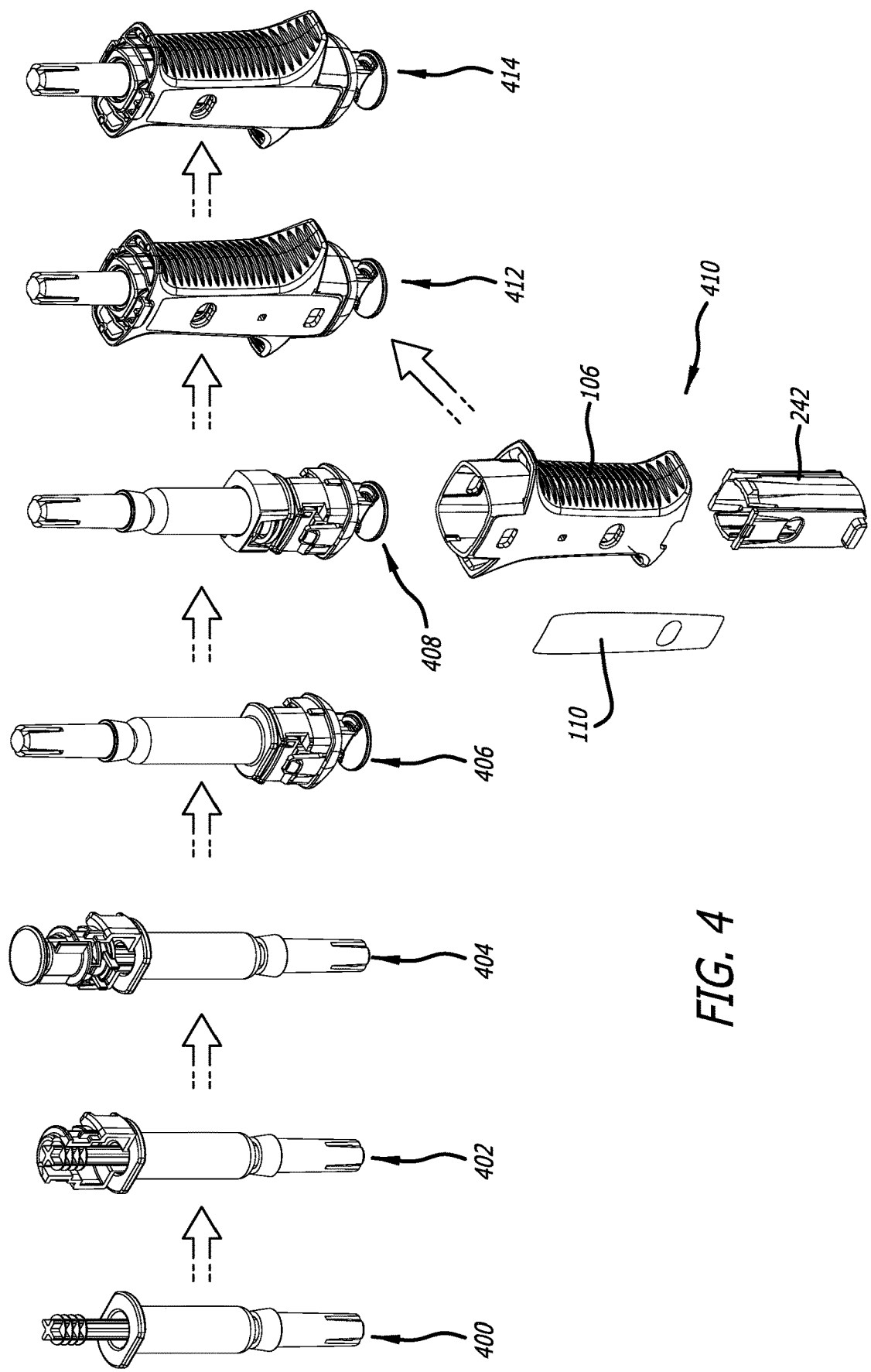
FIG. 4 illustrates a non-limiting assembly method for the syringe devices as described herein.

FIG. 4 illustrates a non-limiting assembly method for the syringe devices as described herein. As a first step 400, a syringe is filled with a desired drug, and if desired, an appropriately sized gas bubble. In some embodiments, a bubble is not included and/or is not needed. A plunger rod is then screwed to the syringe's stopper. In a second step 402, a spacer is added around the plunger rod. In a next step 404, the actuator is attached opposite the spacer. A top is then placed on the spacer and actuator to complete the plunger assembly in a fourth step 406. A spring and a syringe stop ring are then slid down around the syringe body until they meet the syringe's flange in a fifth step 408.

Separately, in step 410 a needle guard is added to an empty encasement and retracted into the encasement. Appropriate label(s) are added to the encasement in step 410 as well.

Next, in step 412, the encasement is then slid over the syringe that includes the plunger assembly and snapped into place attached to the top's teeth. Any additional labels can be added to complete the assembly of the herein described syringe in step 414.

In some embodiments, the syringe devices are single use and/or disposable. Such single use devices are generally used for a single treatment and then discarded in an appropriate manner consistent with health regulations.

In some embodiments, the contents of syringe devices and devices themselves are sterile. Sterile syringe devices can be obtained by sterile filling and device assembly or by sterilizing the syringe devices after assembly. The syringe devices described herein can be sterilized using conventional sterilization techniques such as, but not limited to gamma irradiation techniques.

Syringe devices described herein can be packaged for distribution to users. Packaging can take on forms that can at least partially encase or cover portions of the syringe devices that may be conducive to interference. In one embodiment, syringe devices can be fully encased.

An example case for syringe device 100 is illustrated in FIGS. 5A-C, 6, and 7. Case 500 can be opened and closed on a hinge 502 and a locking mechanism 504. Locking mechanism 504 can allow for a single use or multiple uses. In one embodiment, locking mechanism 504 can be a hook and catch mechanism.

Case 500 can be shaped to fit a single syringe device. FIG. 5C illustrates a syringe device 100 loaded in case 500. In one embodiment, case 500 can be configured to be at least as long as syringe device 100 from the tip of a needle cover to the top of an actuator finger surface in a ready to use configuration. In other embodiments, case 500 can be configured to hold syringe device 100 in an angled configuration.

Figure 7:
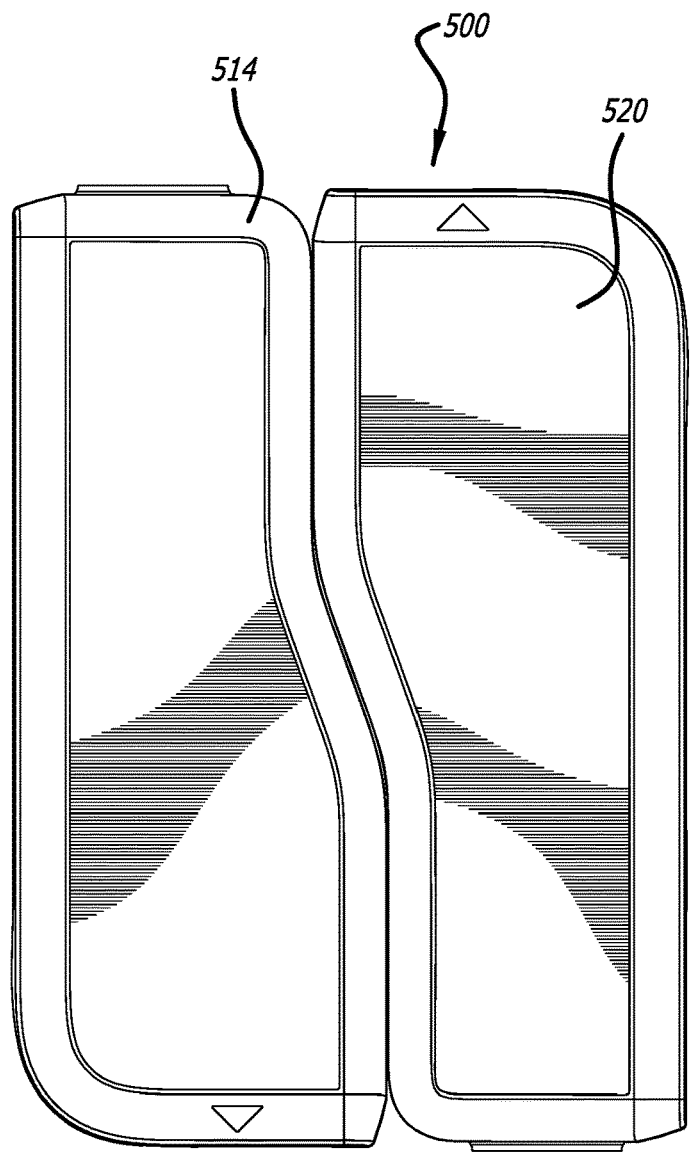
FIG. 7 illustrates two cases coupled together to form a single unit.

Allowing syringe device 100 to sit at angle 506 can allow for case 500 to have a wider bottom portion 508 than top portion 510. Because top portion 510 and bottom portion 508 are not the same, a non-linear edge 512 is created. A second case 514 as illustrated in FIG. 7 can be spun 180 degrees and the non-linear edge of each can be matched up.

Figures 5A, 5B:
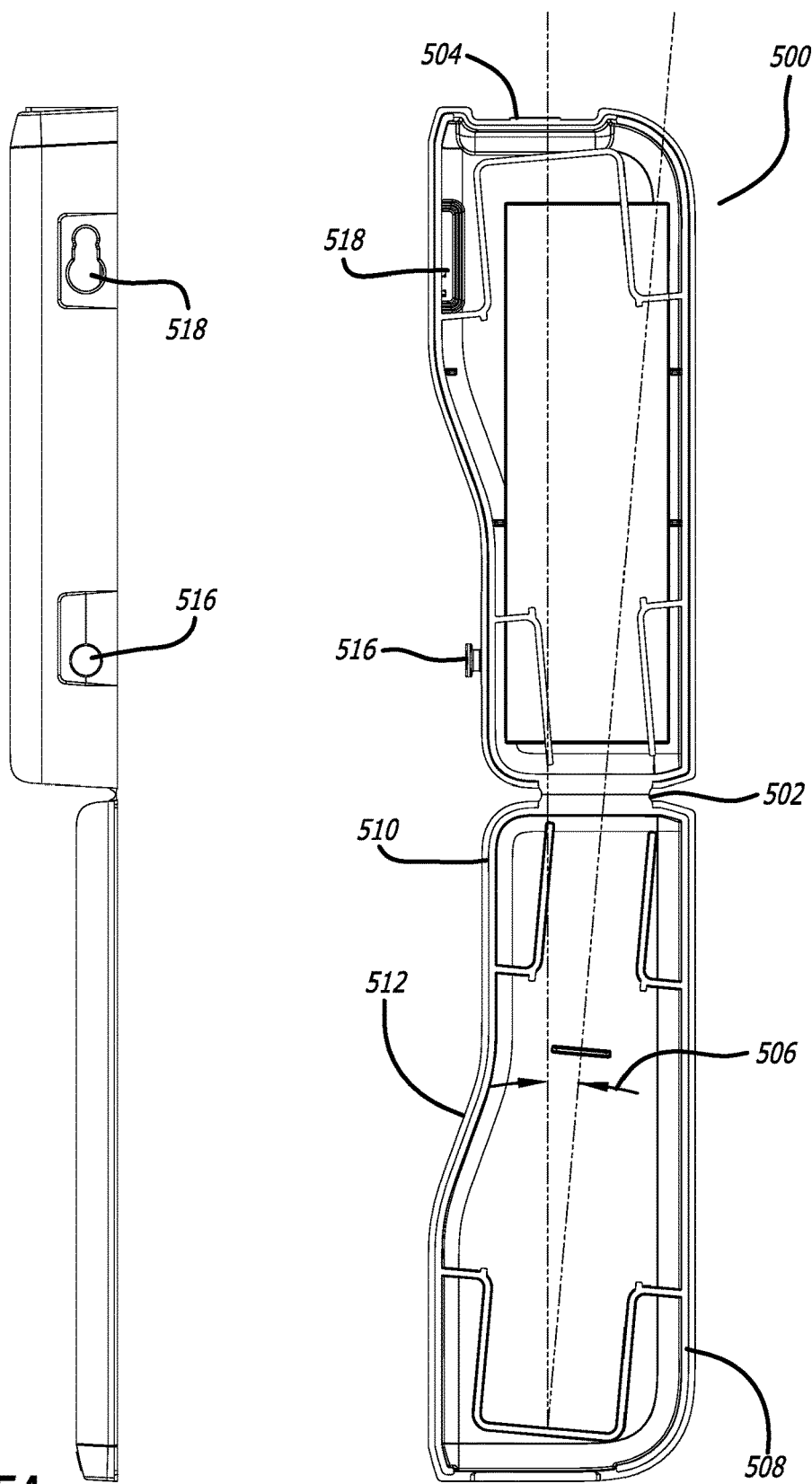
FIG. 5A illustrates a side view of a case for the syringe devices described herein in an open configuration.
FIG. 5B illustrates a top view of a case for the syringe devices described herein in an open configuration without a syringe device.
Figure 5C:
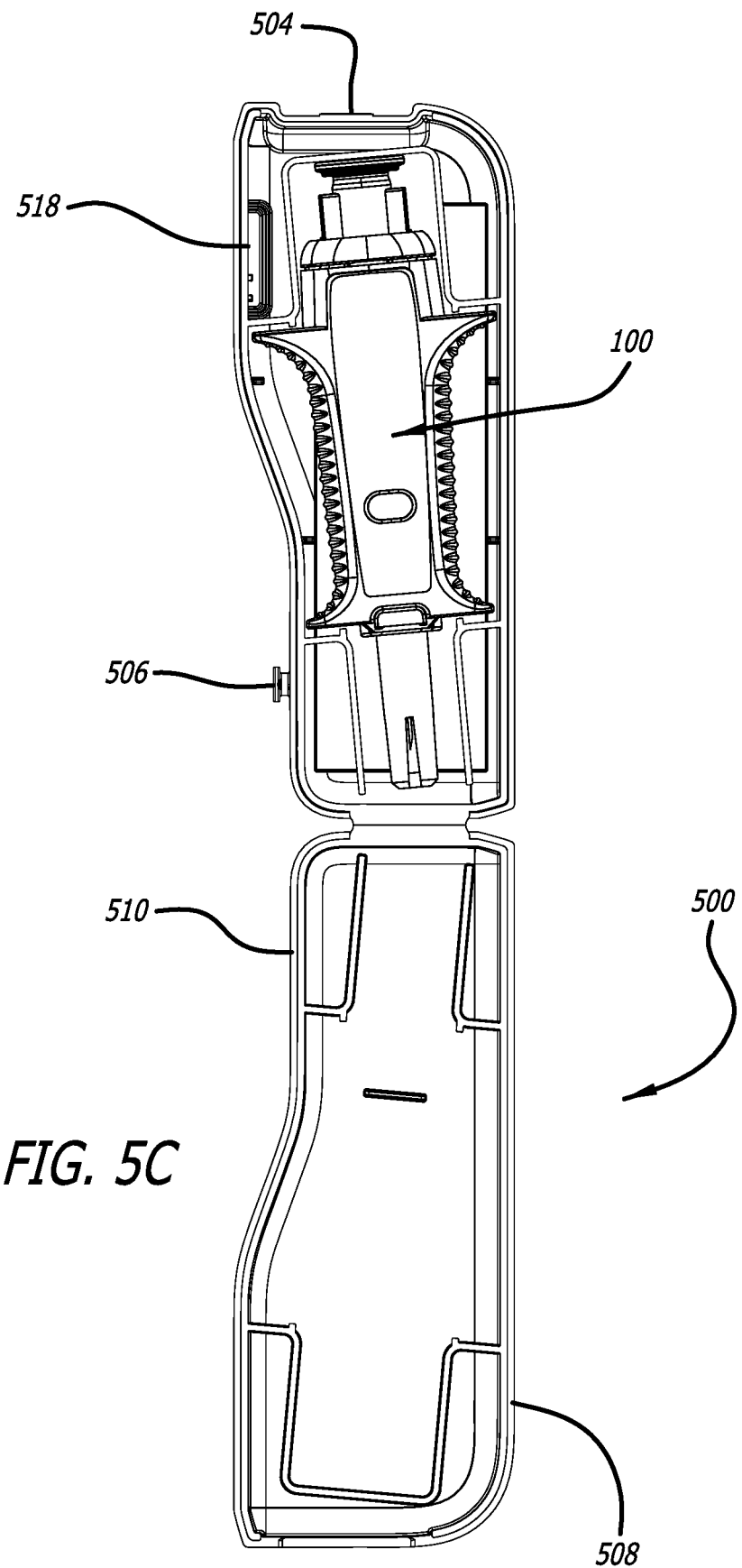
FIG. 5C illustrates a top view of a case for the syringe devices described herein in an open configuration including a syringe device loaded therein.
Figure 6:
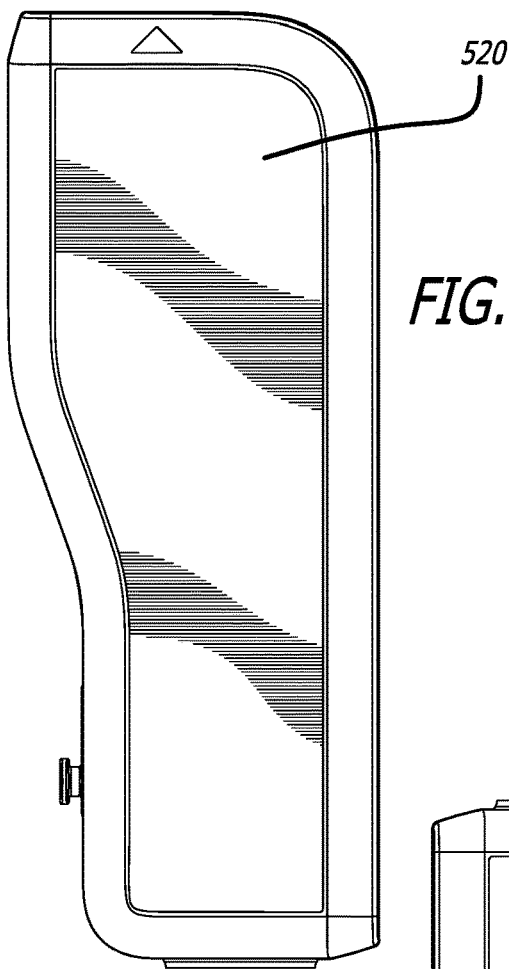
FIG. 6 illustrates a case of FIGS. 5A-C in a closed configuration.

Angle 506 shown in FIG. 5B can be about 3 degrees, about 4 degrees, about 5 degrees, about 6 degrees, about 7 degrees, about 8 degrees, about 9 degrees, about 10 degrees, between about 3 degrees and about 8 degrees, between about 4 degrees and about 6 degrees, or at least about 3 degrees. In one embodiment, angle 506 is about 5 degrees.

In some embodiments, each case can include a fastening nub 516 and a receiving orifice 518 can be included on non-linear edge 512. Receiving orifice 518 can have a key hole configuration allowing for fastening nub 516 to be inserted into the larger portion of the key hole and slid and locked into place. Thus, when case 500 and second case 514 are mated, two sets of fastening nubs and receiving orifices can be used to hold the two cases together.

Fitting two cases together can allow a user to carry a single dose of a drug in case of an emergency and have a second dose close at hand in case a second dosage is needed. FIG. 7 illustrates two cases joined together. Angling the syringe device within a case allows for the overall length of the case to be reduced. The extra width of a case is mitigated by the ability to join two cases together with an overall joined width that is less than double the width of a single case. Thus, this joined configuration can meet a need to have multiple dosages with a small physical footprint.

Case 500 (or second case 514) can include one or more labels that provide information about the drug or drugs being delivered via an enclosed syringe device. As illustrated in FIGS. 5A-C, 6, and 7, case label 520 can cover substantially an entire surface of case 500. However, in other embodiments, case label 520 may cover less than an entire surface of case 500 or multiple labels can be used instead of one large label. In fact, in some embodiments, any number of labels of any shapes can be used to label a case as needed.

Cases can be formed of any appropriate material that can house the described syringes through loading, shipping, regular carrying by patients, and the like without damage to an enclosed syringe device. In some embodiments, cases can be formed of a polymeric material such as a thermoplastic. In one embodiment, cases can be formed of a polypropylene material. Cases can be extruded, blow molded, or the like.

Cases can be textured on portions of their surface in order to allow a user to easily grip a case(s). In one embodiment, cases can be textured using MT-11010.

Cases can have identification markers such as an arrow(s) indicating which side of the case is used to open it. In some embodiments, raised features can be used so that a user when administering an injection to a patient in an emergency drug overdose can open the case without actually focusing on it. Also, in some embodiments, by including a non-linear edge, tactile opening of the case can be accomplished knowing that the thicker end of the case is opened.

Further, cases can be color coded to indicate a particular drug. Cases can be color coded to indicate the order of use of the enclosed syringe device.

Figure 8:
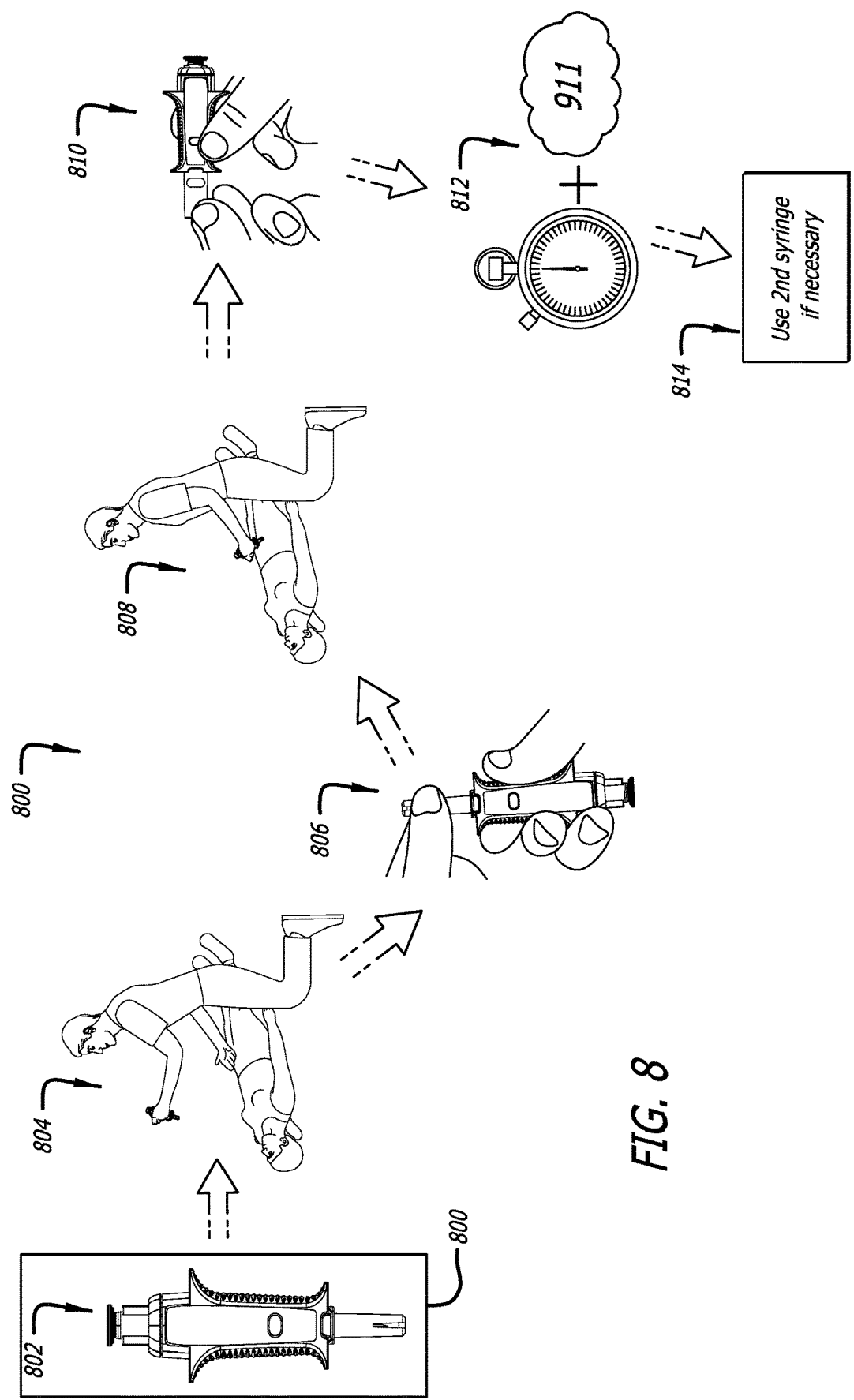
FIG. 8 illustrates a non-limiting method of using the herein described syringe devices.

An example use of a syringe device as described herein is illustrated in FIG. 8. FIG. 8 is illustrated in the context of the non-limiting use of naloxone and illustrates an instruction insert 800. Insert 800 includes a diagram 802 of the syringe device itself, labeling the various use parts of the device for a clear illustration for a user during an emergency drug overdose situation (parts not labeled for simplicity).

As a first step 804, the user is instructed to remove a syringe device from a container and examine the patient for an appropriate injection site. In one embodiment, the injection can be on the thigh. Although described as using a thigh, other injection sites can be used, such as but not limited to the arm, stomach, buttocks, abdomen, and the like. In some embodiments, injections can be made into muscles.

As a second step 806, a user is instructed to remove the needle cap with the syringe device pointing up.

As a third step 808, a user is shown how to properly hold the syringe device for injection. The user is instructed to inject the patient and put the needle in until it is no longer visible. The plunger (actuator) is pushed until it stops and clicks. The audible click is an indication to the user that the drug has been fully injected. The user is instructed to leave the needle in the skin for an additional two seconds to allow proper absorption. Further, the user is told that excess liquid will remain in the syringe device.

The user is instructed in a forth step 810 to remove the needle and slide the needle guard over the needle. The user then places that syringe device back in the case and snaps the case closed.

Optionally, the user is instructed to massage the location for about 10 seconds. In other embodiments, longer or shorter massages may be required, such as but not limited to, about 5 seconds, about 15 seconds, about 20 seconds, about 25 seconds, about 30 seconds, between about 5 seconds and about 20 seconds, between about 10 seconds and about 20 seconds, at least about 5 seconds, or at least about 10 seconds.

As a fifth step 812 the user is instructed to wait a given time period to determine if the injection has been effective. This time period can be at least about 10 seconds, at least about 20 seconds, at least about 30 seconds, at least about 1 minute, or at least about 5 minutes. Effectiveness can manifest in events including a sensed heartbeat, a stronger heartbeat, breathing, movement, or the like.

The user is instructed to seek medical help and/or to call an emergency line (e.g., 911). The user is told to inform the medical help that they just administered an injection of naloxone. The user is further instructed to give the used needle case including the used syringe device to the medical workers when they arrive.

If the injection is ineffective, the user is told to use the second syringe device if needed as a sixth step 814.

The user is instructed that seeking medical help and/or to calling an emergency line (e.g., 911) can occur at any time during the process. The user need not wait until step five to seek emergency medical help.

In some embodiments, the syringe devices described herein can be provided as systems or kits. These systems and kits can include a syringe device enclosed in a container with instructions for use.

In other embodiments, systems and kits can include two syringe devices each enclosed in a separate container each with instructions for use. In still other embodiments, a system or kit can include two syringe device filled containers that are connected as described herein.

In one embodiment, systems and kits can include a syringe device filled with a therapeutic amount of a drug enclosed in a container with instructions for use. In other embodiments, systems and kits can include two syringe devices each filled with a therapeutic amount of a drug, each enclosed in a separate container, and each including instructions for use. In still other embodiments, a system or kit can include two syringe devices filled with a therapeutic amount of a drug in containers that are connected as described herein.

In one embodiment, systems and kits can include a syringe device filled with a therapeutic amount of an opioid antagonist enclosed in a container with instructions for use. In other embodiments, systems and kits can include two syringe devices each filled with a therapeutic amount of opioid antagonist, each enclosed in a separate container, and each including instructions for use. In still other embodiments, a system or kit can include two syringe devices filled with a therapeutic amount of opioid antagonist in containers that are connected as described herein.

In one embodiment, systems and kits can include a syringe device filled with a therapeutic amount of naloxone enclosed in a container with instructions for use. In other embodiments, systems and kits can include two syringe devices each filled with a therapeutic amount of naloxone, each enclosed in a separate container, and each including instructions for use. In still other embodiments, a system or kit can include two syringe devices filled with a therapeutic amount of naloxone in containers that are connected as described herein.

In some embodiments, a syringe device(s) can be distributed to a patient without a drug included within it. The syringe device(s) can be loaded into cases. These syringe devices can be used as training devices to allow a potential user to understand how the syringe device works so that in an emergency overdose situation, they will be ready to use an actual syringe device. In some embodiments, a training device may not include a needle so that a trainee can partake in all the steps except the needle injection portion.

In some embodiments, the syringe devices described herein can prevent a user from unscrewing the plunger rod from the stopper. This prevention ability of the presently described syringe devices can disallow a change in travel stroke and hence delivered drug volume of traditional syringes. Further, the syringe devices described herein can prevent a user moving the plunger rod and/or stopper thereby affecting the delivery volume of a drug filled syringe device. Further still, the presently described syringe devices can prevent a user from pulling out and/or back the stopper/plunger rod thereby altering the delivered volume and the purity of the drug.

As discussed, the presently described syringe devices can provide tactical feedback to alert a user of a complete drug dose delivery. Typical syringes only allow a tactical feedback when the stopper and/or plunger reach an end stop.

The presently described syringe devices can also prevent a user from modifying the plunger and/or stopper to alter the amount of preset drug delivery. The present syringe devices can deliver a preset drug dosage without intervention by the user that can alter an amount of drug delivered.

The presently described syringe devices can prevent sub-optimal drug injections by preventing unexpected syringe delivery orientations. Syringes can generally provide optimal delivery of drugs when oriented in a particular angle for injection. The present syringe devices can provide a surface that can press against the injection site and effectively hold the syringe devices at a predetermined angle for injection.

In some embodiments, the presently described syringe devices do not include electronics. In some embodiments, the presently described syringe devices do not include a battery or batteries. In some embodiments, the presently described syringe devices do not include a circuit board. In some embodiments, the presently described syringe devices do not include an energy source to move the actuator.

The following represent non-limiting embodiments.

Embodiment 1: An emergency syringe device comprising a syringe including a therapeutic dose of at least one opioid antagonist, and a stopper; and a plunger assembly including a plunger rod, an actuator, and a spacer, wherein the plunger assembly is configured to move the stopper a predetermined distance without a user touching the plunger rod or being able to retract the plunger rod.

Embodiment 2: The syringe device of Embodiment 1, wherein the plunger assembly is configured to provide substantially identical doses of the at least one opioid antagonist even if more or less opioid antagonist is provided in the syringe by moving the stopper a predetermined distance.

Embodiment 3: The syringe device of Embodiment 1 or 2, further including an encasement configured to house the syringe.

Embodiment 4: The syringe device of Embodiment 1, 2, or 3, wherein the encasement includes a window configured to allow the user to view the at least one opioid antagonist in the syringe.

Embodiment 5: The syringe device of Embodiment 1, 2, or 3, wherein the encasement includes a needle guard configured to allow the user to cover the needle after use.

Embodiment 6: The syringe device of Embodiment 1, 2, 3, 4, or 5, wherein the at least one opioid antagonist is naloxone, a salt thereof, a derivative thereof, or a prodrug thereof.

Embodiment 7: The syringe device of Embodiment 1, 2, 3, 4, 5, or 6, wherein the at least one opioid antagonist is naloxone.

Embodiment 8: The syringe device of Embodiment 1, 2, 3, 4, 5, 6, or 7, wherein the syringe device is configured to deliver about 5 mg of naloxone or a salt thereof.

Embodiment 9: The syringe device of Embodiment 1, 2, 3, 4, 5, 6, or 7, wherein the syringe device is configured to deliver about 15 mg of naloxone or a salt thereof.

Embodiment 10: The syringe device of Embodiment 1, 2, 3, 4, 5, 6, 7, 8, or 9, wherein the actuator and the spacer are configured to be secured around the plunger rod.

Embodiment 11: The syringe device of Embodiment 1, 2, 3, 4, 5, 6, 7, 8, 9, or 10, wherein the actuator includes a finger depression location.

Embodiment 12: The syringe device of Embodiment 1, 2, 3, 4, 5, 6, 7, 8, 9, 10, or 11 configured for use in an opioid overdose.

Embodiment 13: A method for administering a therapeutic dose of at least one opioid antagonist, the method comprising advancing a stopper through a syringe including the therapeutic dose of the at least one opioid antagonist; wherein the stopper is only advanced a predetermined distance by a plunger assembly including a plunger rod, an actuator, and a spacer, wherein the plunger assembly is configured to move the stopper without a user touching the plunger rod.

Embodiment 14: The method of Embodiment 13, wherein the syringe is housed in an encasement.

Embodiment 15: The method of Embodiment 13 or 14, wherein the encasement includes a window configured to allow the user to view the at least one opioid antagonist in the syringe.

Embodiment 16: The method of Embodiment 13 or 14, wherein the encasement includes a needle guard configured to allow the user to cover a needle after use.

Embodiment 17: The method of Embodiment 13, 14, 15, or 16, wherein the at least one opioid antagonist is naloxone, a salt thereof, a derivative thereof, or a prodrug thereof.

Embodiment 18: The method of Embodiment 13, 14, 15, 16, or 17, wherein the at least one opioid antagonist is naloxone.

Embodiment 19: The method of Embodiment 13, 14, 15, 16, 17, or 18, wherein the actuator and the spacer are configured to be secured around the plunger rod and provide the predetermined distance.

Embodiment 20: The method of Embodiment 13, 14, 15, 16, 17, 18, or 19, wherein the actuator and the spacer are configured to provide the predetermined distance between a start point and an end point.

Embodiment 21: The method of Embodiment 13, 14, 15, 16, 17, 18, 19, or 20, wherein the advancing the stopper the predetermined distance is configured to deliver about 5 mg of naloxone or a salt thereof.

Embodiment 22: The method of Embodiment 13, 14, 15, 16, 17, 18, 19, 20, or 21, wherein the advancing the stopper the predetermined distance is configured to deliver about 15 mg of naloxone or a salt thereof.

Example 1

Emergency Naloxone Administration

A 45 year old female suffers from frequent heroin use. After injecting a large dose of heroin intravenously at a party, the female begins to show symptoms of overdose and becomes unconscious. Her heart rate slows and her breath becomes shallow. An onlooker at the party calls 911. The onlooker finds a kit of two naloxone filled syringe devices housed in separate connected cases stocked in the locations first aid kit. He opens one case and removes the syringe device.

An injection area is determined on the female's thigh. He removes the needle cap, inserts the needle into the female's thigh in the selected area, and pushes the plunger until he hears a click. He leaves the needle in the female's thigh for an additional two seconds. He then removes the needle from the female's thigh, slides down the needle cap, places the syringe device back in the container, and shuts the container.

The female slowly regains consciousness. Medical emergency personnel arrive shortly thereafter and transport the female to a local emergency room for further treatment.

Example 2

Emergency Naloxone Aided Injection

A 65 year old man is depressed and ingests a bottle of prescription opioids, thus overdosing himself. The man's wife finds the man barely conscious. The wife calls 911 while she pulls out a kit of two naloxone filled syringe devices housed in separate connected cases. She pops open one case and removes the syringe device.

She selects an injection area on the man's thigh. She removes the needle cap, inserts the needle into the man's thigh in the selected area, and pushes the plunger until she hears a click. She then removes the needle from the man's thigh, slides down the needle cap, places the syringe device back in the container, and shuts the container.

She notices that the injection has little effect on the man. Thus, she pops open the second case and removes the syringe device inside. She repeats injection with the second device. She again removes the needle from the man's thigh, slides down the needle cap, places the syringe device back in the container, and shuts the container.

The man slowly regains consciousness. Medical emergency personnel arrive shortly thereafter and transport the man to a local emergency room for further treatment.

Example 3

In Example 1 and Example 2, each syringe in the kit includes 5 mg of naloxone.

Example 4

In Example 1 and Example 2, each syringe in the kit includes 2.5 mg of naloxone.

Example 5

In Example 1 and Example 2, each syringe in the kit includes 10 mg of naloxone.

Example 6

In Example 1 and Example 2, each syringe in the kit includes 15 mg of naloxone.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An emergency syringe device comprising:
   a syringe including a therapeutic dose of at least one opioid antagonist, and a stopper; and
   a plunger assembly including a plunger rod, an actuator including at least one guide rail, and a spacer, wherein the at least one guide rail travels against a front surface of the spacer,
   wherein the plunger assembly is configured to move the stopper a predetermined distance without a user touching the plunger rod or being able to retract the plunger rod.

2. The syringe device of claim 1, wherein the plunger assembly is configured to provide substantially identical doses of the at least one opioid antagonist even if more or less opioid antagonist is provided in the syringe by moving the stopper a predetermined distance.

3. The syringe device of claim 1, further including:
   an encasement configured to house the syringe.

4. The syringe device of claim 3, wherein the encasement includes a window configured to allow the user to view the at least one opioid antagonist in the syringe.

5. The syringe device of claim 3, wherein the encasement includes a needle guard configured to allow the user to cover a needle associated with the syringe after use.

6. The syringe device of claim 1, wherein the at least one opioid antagonist is naloxone, a salt thereof, a derivative thereof, or a prodrug thereof.

7. The syringe device of claim 1, wherein the at least one opioid antagonist is naloxone.

8. The syringe device of claim 6, wherein the syringe device is configured to deliver about 5 mg of naloxone or a salt thereof.

9. The syringe device of claim 6, wherein the syringe device is configured to deliver about 15 mg of naloxone or a salt thereof.

10. The syringe device of claim 1, wherein the actuator and the spacer are configured to be secured around the plunger rod.

11. The syringe device of claim 1, wherein the actuator includes a finger depression location.

12. The syringe device of claim 1 configured for use in an opioid overdose.

13. A method for administering a therapeutic dose of at least one opioid antagonist, the method comprising:
    providing an emergency syringe device;
    advancing a stopper on the syringe device through a syringe including the therapeutic dose of the at least one opioid antagonist;
    wherein the stopper is only advanced a predetermined distance by a plunger assembly including a plunger rod, an actuator including at least one guide rail, and a spacer, wherein the at least one guide rail travels against a front surface of the spacer,
    wherein the plunger assembly is configured to move the stopper without a user touching the plunger rod.

14. The method of claim 13, wherein the syringe is housed in an encasement.

15. The method of claim 14, wherein the encasement includes a window configured to allow the user to view the at least one opioid antagonist in the syringe.

16. The method of claim 14, wherein the encasement includes a needle guard configured to allow the user to cover a needle after use.

17. The method of claim 13, wherein the at least one opioid antagonist is naloxone, a salt thereof, a derivative thereof, or a prodrug thereof.

18. The method of claim 17, wherein the at least one opioid antagonist is naloxone.

19. The method of claim 13, wherein the actuator and the spacer are configured to be secured around the plunger rod and provide the predetermined distance.

20. The method of claim 13, wherein the actuator and the spacer are configured to provide the predetermined distance between a start point and an end point.

21. The method of claim 13, wherein the advancing of the stopper the predetermined distance is configured to deliver about 5 mg of naloxone or a salt thereof.

22. The method of claim 13, wherein the advancing of the stopper the predetermined distance is configured to deliver about 100 mg of naloxone or a salt thereof.

* * * * *